United States Patent [19]

Smith

[11] Patent Number: 6,037,784
[45] Date of Patent: Mar. 14, 2000

[54] RESISTIVITY MEASURING APPARATUS HAVING TRANSMITTER AND RECEIVER WITH POWER LEVEL SIGNALS

[75] Inventor: Kenneth R. Smith, Sunnyvale, Calif.

[73] Assignee: Geometrics, San Jose, Calif.

[21] Appl. No.: 09/270,132

[22] Filed: Mar. 16, 1999

[51] Int. Cl.[7] .......................... G01N 27/02; G01K 27/02
[52] U.S. Cl. ....................... 324/694; 324/683; 324/709; 324/639
[58] Field of Search ................................. 324/639, 640, 324/664, 667, 693, 694, 707, 709, 713, 715, 717, 674, 681, 683

[56] References Cited

U.S. PATENT DOCUMENTS

| | | | |
|---|---|---|---|
| 4,220,915 | 9/1980 | Kawamoto et al. | 324/639 |
| 5,136,252 | 8/1992 | Witt | 324/715 |
| 5,386,196 | 1/1995 | Jones et al. | 324/667 |
| 5,428,296 | 6/1995 | Champagne et al. | 324/696 |
| 5,570,030 | 10/1996 | Wightman | 324/694 |
| 5,841,282 | 11/1998 | Christy et al. | 324/694 |

OTHER PUBLICATIONS

Geometrics OhmMapper—Resistivity Mapping™—first distribution in Feb. 1999.

V.M. Timofeev, (Vsegingeo, Moscow, Russia), "Electric and Electromagnetic Profiling With Ground Capacitive Line-Antennas"—paper presented at a seminar in USSR or in Russia, in or about 1995.

*Primary Examiner*—Diep N. Do
*Attorney, Agent, or Firm*—Townsend and Townsend and Crew LLP; Henry K. Woodward

[57] ABSTRACT

Material resistivity measuring apparatus includes a transmitter for transmitting a measurement frequency current through the material to a receiver spaced from the transmitter. The transmitter includes a power amplifier wherein the measurement frequency current is amplified in discrete steps depending upon resistivity of the material. The current level of the transmitter is transmitted to the receiver by modulating the measurement frequency current by a modulation signal whose phase is indicative of power level. The measurement frequency current can be modulated by a second modulating signal which provides a reference phase for the first modulating signal.

32 Claims, 4 Drawing Sheets

RESISTIVITY MEASURING APPARATUS HAVING TRANSMITTER AND RECEIVER WITH POWER LEVEL SIGNALS

BACKGROUND OF THE INVENTION

This invention relates generally to material resistivity measuring apparatus in which an electrical signal is transmitted through the material to a receiver, and more particularly the invention is directed to such transmitter and receiver apparatus in which the level of transmitter current is communicated to the receiver for use in material resistivity determination.

The resistivity of a material can be determined by passing a current through the material at one pair of electrodes and measuring received voltage at another pair of electrodes. This is a common practice in geophysical measurements in which a transmitter applies an alternating current to the ground through a first electrode structure, and voltage at the transmission frequency is detected by a receiver through a second electrode structure on the ground and spaced from the first electrode structure. The detected current is a measure of soil resistivity, assuming the transmitter power level (voltage, current) is known.

The resistivity of soils varies over a wide range. Moist soil rich in conductive material such as clay and ferrous material will have a lower resistivity and higher current conduction as compared to a dry sandy soil, for example. Small currents may be sufficient for resistivity measurements in dry sandy soils, but higher current will be required for lower resistivity soils.

Thus, the transmitter must be able to operate at different current levels. In capacitively coupled resistivity measurement systems, the current generated by the transmitter is an AC current at some fixed frequency somewhere in the range from a few KHz to several tens of KHz. The transmitter may be producing as much as 1,000 volts at this frequency to achieve the requisite current through the soil. This is required since the coupling impedance from the electrode to the soil must be much greater than resistance of the soil just below the electrode in order for measurements to be accurately determinative of soil resistivity.

Accordingly, in determining soil resistivity the receiver must be aware of the transmitter current level. However, the only external electrical connections on either the transmitter or the receiver are the electrodes which are placed on and capacitively coupled to the ground. Any other electrical wires would capacitively couple to the electrodes and to the ground thus changing the geometry of the measurement.

The present invention allows transmission of power level settings from the transmitter to the receiver using only the electrodes of the transmitter and receiver.

SUMMARY OF THE INVENTION

The present invention is a method and structure for communicating the current level of a transmitter to a receiver in resistivity measuring apparatus for a material such as soil. The transmitter applies a measurement frequency signal through a variable power amplifier to transmitter electrodes. The measurement frequency signal is modulated by a first modulation signal having a phase indicative of current level. The receiver receives the transmitted signal and detects the first modulation signal, and transmitter power level is then determined from the phase of the detected modulation signal.

In a preferred embodiment the measurement frequency signal is modulated also by a second modulation signal which provides a phase reference for the phase of the first modulation signal. In one embodiment the first modulation signal is 4 Hz and the second modulation signal is 2 Hz. Phase of the 4 Hz signal is varied in eight steps from 0° to 315° to correspond to eight different current levels of the transmitter. Power level of the power amplifier is set by a servo loop in the transmitter which senses a measure of current from the variable power amplifier and adjusts the variable power amplifier to regulate the current to be correct for the selected transmitter current level.

In accordance with one feature of the invention the phases corresponding to two adjacent power level settings are separated by at least one additional phase setting so that the detected phase can be immune from noise spikes in the detected signal. Thus any phase shift of the detected signal which changes by only one discrete step can be ignored as resulting from noise.

The invention and objects and features thereof will be more readily apparent from the following detailed description and appended claims when taken with the drawings.

DETAILED DESCRIPTION OF ILLUSTRATIVE EMBODIMENTS

Figure 1:
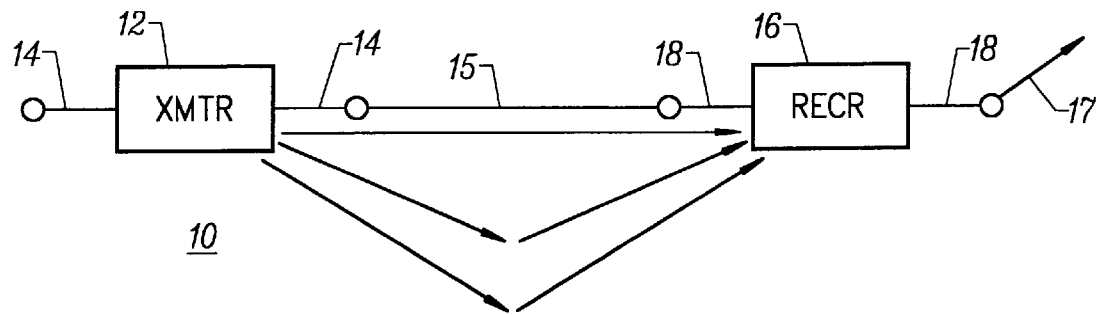
FIG. 1 illustrates resistivity measuring apparatus for detecting the resistivity of soil.

Referring now to the drawings, FIG. 1 illustrates resistivity measuring apparatus for determining the resistivity of soil 10, the apparatus including a signal transmitter 12 having electrodes 14 coupled to soil 10 and a receiver 16 having electrodes 18 coupled to soil 10 at a point spaced from transmitter 12. Transmitter 12 and receiver 16 are connected by an non-conductive tow member or rope 15 so that the transmitter and receiver can be pulled over the ground as indicated at 17. Resistivity of the soil is determined by applying a signal at a predetermined measurement frequency through electrodes 14 to the soil and then detecting the voltage of a received signal by receiver 16 through electrodes 18. As noted above, the signal generated by the transmitter produces an AC current at a fixed frequency in the range from a few KHz to several tens of KHz at a voltage level up to 1,000 volts. The detected voltage received by receiver 16 through electrodes 18 can be from on the order of 1 microvolt to 1 volt. As further noted above, the transmitter current must be variable over a range of more than 10 to 1 since the requisite current level applied to the soil is dependent on the resistivity of the soil.

In accordance with the invention the measurement frequency signal transmitted by a the transmitter is modulated by modulation signal having a phase which is indicative of the current setting in the transmitter. Thus, a determination of soil resistivity can be made at the receiver based upon detected measurement frequency voltage and the known current level of the transmitter.

Figure 2A:
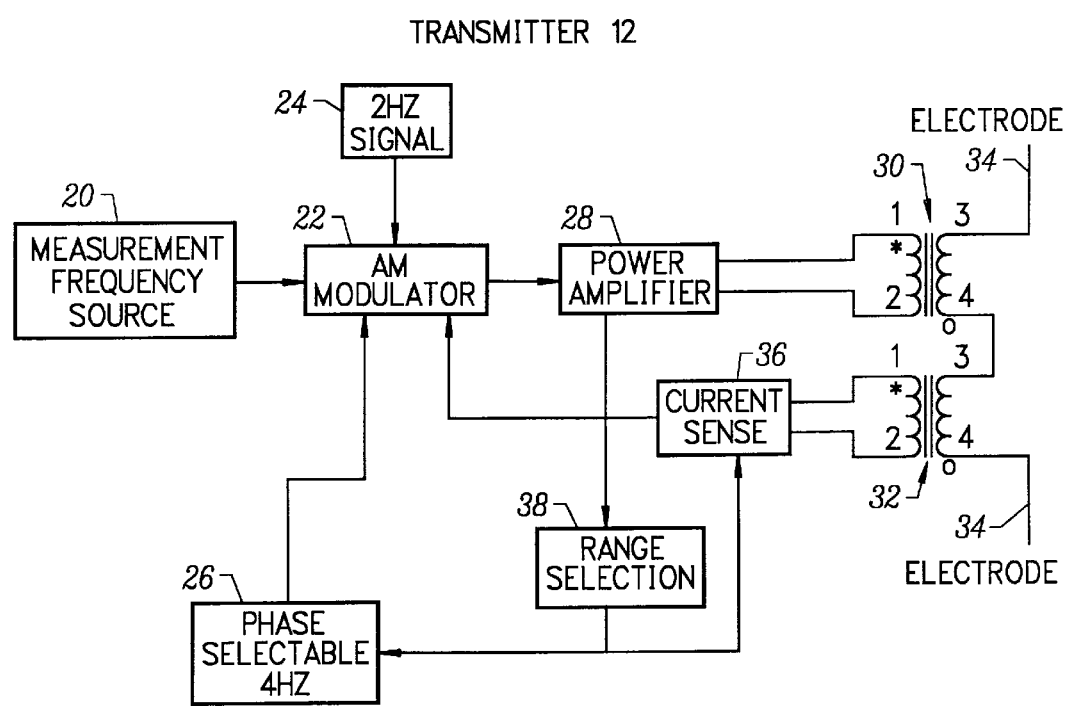
FIGS. 2A and 2B are functional block diagrams of a transmitter and a receiver in the apparatus of FIG. 1.
Figure 2B:
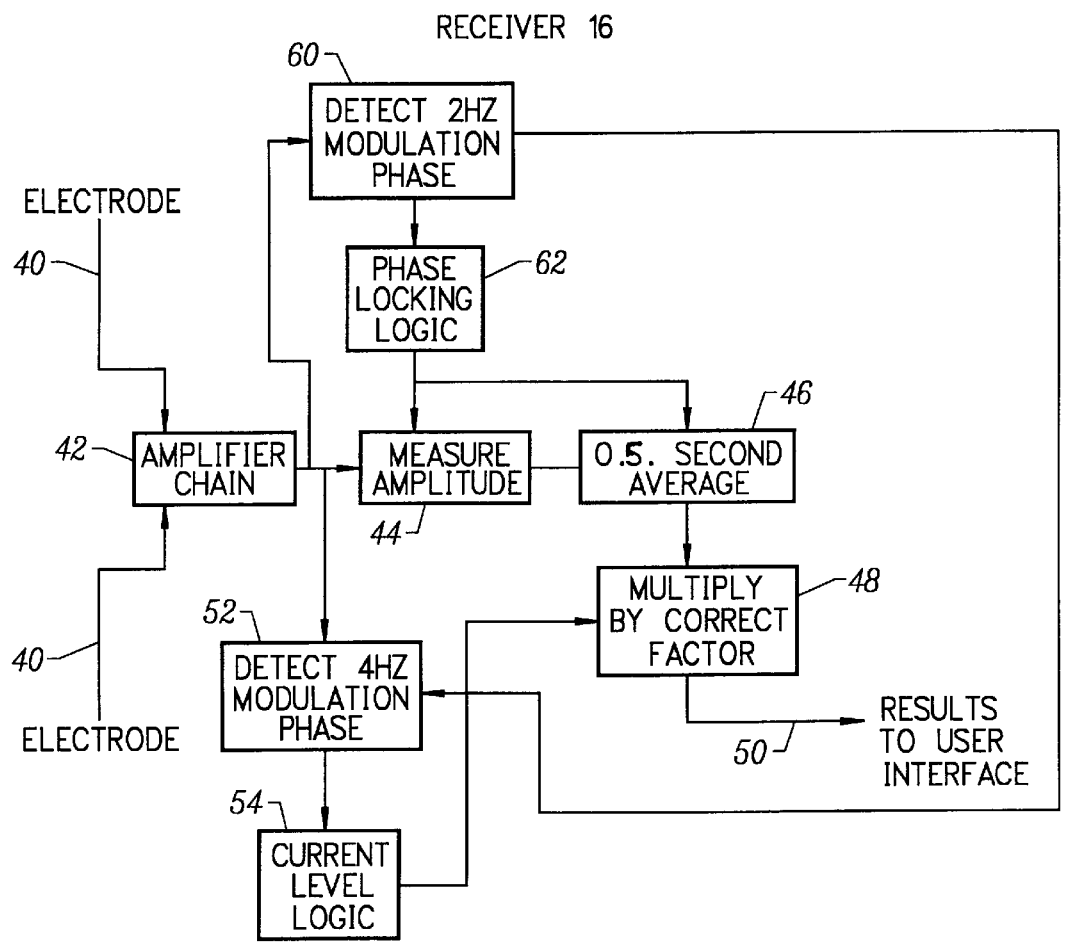

FIGS. 2A and 2B are functional block diagrams of a transmitter and a receiver, respectively, in accordance with one embodiment of the invention. In FIG. 2A a measurement frequency source 20 generates a signal at the desired frequency (up to tens of KHz) which is applied to a modulator 22. In this embodiment modulator 22 is an amplitude modulator which modulates the measurement frequency signal from source 20 by a 2 Hz signal from source 24 and by a 4 Hz signal from source 26. The modulated measurement frequency signal is then applied to a variable power amplifier 28 which amplifies the modulated signal. The output of power amplifier 28 is then coupled through a transformer 30 and transformer 32 to a pair of electrodes 34. Electrodes 34 then apply a current at the modulated measurement frequency to the ground.

A servo loop senses current applied to electrode 34 and controls the power setting of amplifier 28. The servo loop includes a current sensing circuit 36 which senses electrode current through transformer 32 and provides feedback through modulator 22 to power amplifier 28 for establishing a required voltage to cause the desired current to flow. The power level of amplifier 28 is applied to the range selection electronics 38 the output of which controls the phase of the 4 Hz signal from source 26 to correspond to the power level. The current range selection is also communicated to current sensing electronics 36 for establishing a basis for the current sense. Thus, each current setting of transmitter 12 has a corresponding phase on the 4 Hz signal from source 26. The 4 Hz signal along with the 2 Hz phase reference signal from source 24 modulate the measurement frequency signal from source 20 for transmission through electrodes 34.

FIG. 2B is a functional block diagram of the receiver which includes electrodes 40 spaced from electrodes 34 for detecting voltage at the measurement frequency. The sensed voltage is applied through an amplifier 42 and then to an amplitude measurement circuit 44. The measured amplitude is then applied through an averaging circuit 46 to a level correction circuit 48 and then to a user interface at 50.

Circuit 52 detects the 4 Hz modulation signal and the phase thereof which is used by current level logic 54 to determine the current setting of the transmitter. Current level logic 54 then controls the correction factor circuit 48 in accordance with the current setting of transmitter 12.

The 2 Hz modulating signal from transmitter 12 provides a reference phase for the 4 Hz modulating signal. The 2 Hz signal is detected by circuit 60 which then controls the phase of the amplified signal from amplifier 42 through phase locking circuitry 62 which controls the phase of amplitude detector 44 and averaging circuit 46.

As described, the transmitter current is modulated at two frequencies, 2 Hz and 4 Hz. If the measurement interval of the receiver is forced to be in step with the 2 Hz signal from the transmitter and the transmitter is only able to change its current setting at a time that is a boundary between one measurement and the next measurement, the receiver can use its measured average voltage and phase value to accurately determine the soil resistivity. There will not be spurious reading caused by the transmitter changing current levels during a measurement interval of the receiver. The current of the transmitter can be modulated as described without affecting the measurement being made so long as the modulation has no average effect over the measurement interval of the receiver. So long as the amplitude modulation waveform completes an integer number of cycles in a measurement interval of the receiver, the averaging of the signal within the receiver will eliminate the effect thereof. In one embodiment the receiver averages for a half second. Thus frequencies that are multiples of 2 Hz will complete an integer number of cycles in this measurement time.

By using a finite number (e.g. 8) of tightly regulated currents in the transmitter, the problem of noise in the 4 Hz phase measurement is largely removed. The receiver only needs to be able to determine which of the finite number of current levels is in use. Noise only becomes a problem when it is large enough to make this determination impossible.

In practical soil survey applications the transmitter will only need to change current settings on rare occasions. These changes will be only to the next adjacent current setting (e.g. higher or lower). Noise spikes can be suppressed by having the phase values corresponding to two adjacent current settings not being adjacent values of phase. For example, assume the phase follows the following equation:

$$\text{Phase} = (45 \times 3 \times \text{PowerLevel}) \text{MOD } 360$$

If a noise spoke causes the measured phase to be within the range for the next adjacent phase, this will not be the phase for the next adjacent power level. Logic in the receiver detects this invalid change in power level. Since the power level of the transmitter changes only rarely, the receiver can assume that the transmitter power did not change and this assumption will be correct most of the time.

Figure 3:
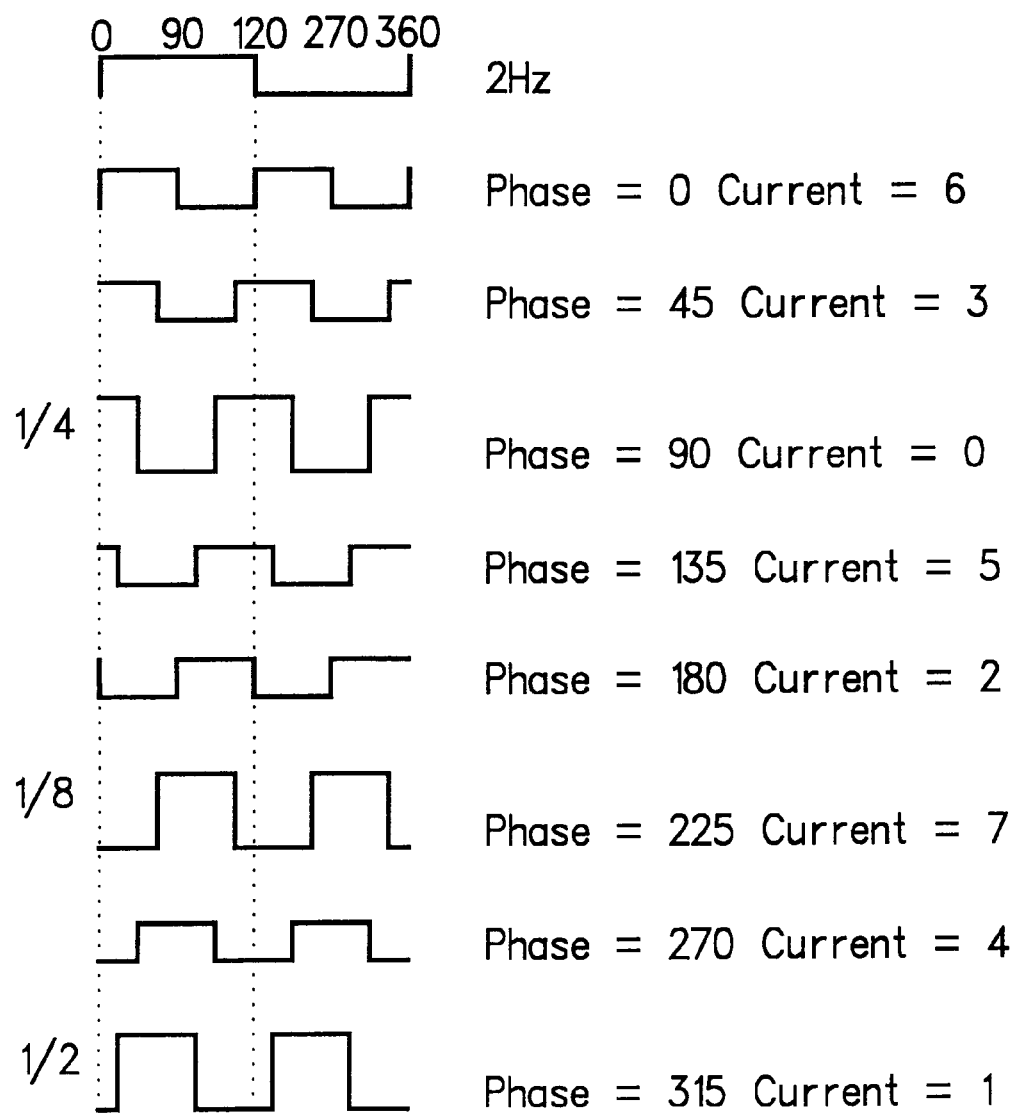
FIG. 3 illustrates phases of two modulating frequency signals in the transmitter of FIG. 2A.

FIG. 3 is a graph illustrating the respective phase of the 4 Hz signal and the power settings of the amplifier. It will be noted that no two adjacent current settings have adjacent phase values.

Figure 4:
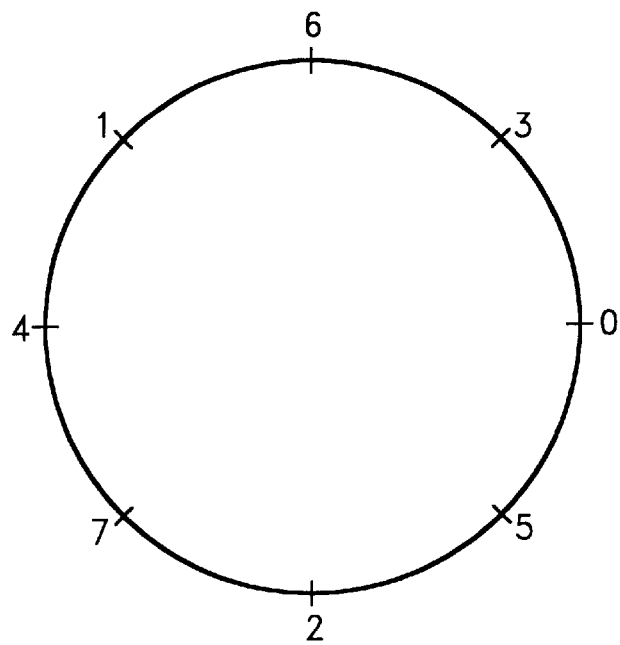
FIG. 4 illustrates current level settings corresponding to the phase of a modulating signal of FIG. 3.

FIG. 4 is an illustration of the 2 Hz reference phase and the 8 phase levels of the 4 Hz signal which are indicative of 8 different power levels of the power amplifier 28. As described above, no two adjacent phase settings correspond to adjacent power settings.

There has been described material resistivity measuring apparatus and a method of communicating power levels of the transmitter to the receiver in such apparatus. While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. Material resistivity measuring apparatus comprising a) a transmitter including
   an AC voltage source producing a signal at a frequency at which a measurement is to be made,
   a modulator for modulating the signal from the AC voltage source,
   a power amplifier for amplifying the signal from the modulator and producing a signal with increased voltage,
   a first electrode apparatus connected to the output of the power amplifier and coupled to the material being measured,
   a sensing circuit for sensing AC current in the first electrode apparatus, and
   a variable phase AC voltage source for applying a first modulating signal, at a phase dependent on the AC current in the first electrode apparatus, to an input of the modulator, b) a receiver including
   a second electrode apparatus coupled to the material being measured and spaced from the first electrode apparatus for receiving modulated AC voltage created by transmitter AC current flowing in the material,
   a detector for detecting the phase of the modulated AC voltage, and apparatus for adjusting the received signal according to current level of the transmitter as determined by the detector.

2. Material resistivity measuring apparatus as defined by claim 1 wherein the modulator provides a discrete number of phases to a modulating voltage for a corresponding discrete number of current levels.

3. The material resistivity measuring apparatus as defined by claim 2 wherein adjacent current levels have corresponding phases which are separated by at least one discrete phase to limit the effect of spurious signals.

4. The material resistivity measuring apparatus as defined by claim 3 wherein the modulating voltage is 4 Hz and the discrete number of phases is eight.

5. The material resistivity measuring apparatus as defined by claim 4 and further including a fixed phase voltage source for generating a second modulating voltage for modulating the measurement frequency voltage in the transmitter and establishing a phase reference measurement interval in the receiver.

6. The material resistivity measuring apparatus as defined by claim 5 wherein the fixed phase is at 2 Hz.

7. The material resistivity measuring apparatus as defined by claim 1 and further including a fixed phase voltage source for generating a second modulating voltage for modulating the measurement frequency voltage in the transmitter and establishing a phase reference measurement interval in the receiver.

8. The material resistivity measuring apparatus as defined by claim 1 wherein the material is soil.

9. The material resistivity measuring apparatus as defined by claim 1 wherein the first and second electrode apparatus each comprises two electrodes.

10. The material resistivity measuring apparatus as defined by claim 9 wherein the electrodes of the first and second electrode apparatus are linearly aligned and the apparatus can be moved along the material surface.

11. The material resistivity measuring apparatus as defined by claim 1 wherein the transmitter further includes a servo loop to control the power level of the variable power amplifier.

12. The material resistivity measuring apparatus as defined by claim 11 wherein the servo loop senses a measure of current from the variable power amplifier.

13. The material resistivity measuring apparatus as defined in claim 12 wherein the servo loop in the transmitter controls the output of the power amplifier by means of a third modulation input to the modulator from the sensing apparatus.

14. In a material resistivity measuring apparatus including a signal transmitter and a signal receiver space from the transmitter, a method of communicating power level of the transmitter to the receiver comprising the steps:
 a) applying a measurement frequency signal through a power amplifier to transmitter electrodes,
 b) modulating the measurement frequency signal by first modulation signal having a phase indicative of current level of the transmitter,
 c) receiving a transmitted signal from the transmitter electrodes and detecting the first modulating signal, and
 d) determining transmitter power level from the phase of the detected first modulating signal.

15. The method as defined by claim 14 wherein step b) includes modulating the measurement frequency signal by a second modulating signal which provides a phase reference for the phase of the first modulation signal.

16. The method as defined by claim 14 wherein the first modulating signal is 4 Hz in frequency and a second modulating signal is 2 Hz in frequency.

17. The method as defined by claim 16 wherein power level of the variable power amplifier is established by a servo loop in the transmitter.

18. The method as defined by claim 17 wherein the servo loop senses a measure of current from the variable power amplifier.

19. Material resistivity measuring apparatus comprising
 a) a transmitter including
  an AC voltage source producing a signal at the frequency at which the measurement is to be made,
  a modulator for modulating the signal from the AC signal source with a first modulation signal,
  a power amplifier for amplifying the signal from the modulator producing a signal with a greater voltage,
  a first electrode apparatus connected to the output of the power amplifier and coupled to the material being measured,
  a sensing apparatus for sensing the AC current flowing into the first electrode apparatus caused by the applied AC voltage, and
  a variable phase AC voltage source for applying a first modulation signal at a phase dependent on the sensed AC current in the first electrode apparatus, to an input of the modulator,
 b) a receiver including
  a second electrode apparatus coupled to the material being measured and spaced from the first electrode apparatus for receiving the AC voltage created by the transmitter AC current flowing in the material,
  a measuring apparatus for measuring the amplitude of the AC voltage received,
  an averaging apparatus for averaging the measured amplitude over a time interval,
  a detecting apparatus for detecting the phase of the first modulation of the received AC voltage,
  a current determining apparatus for determining the current in the first electrode apparatus based on the phase of the AC voltage, and
  a multiplying apparatus for multiplying the output of the averaging apparatus by a factor based on the current in the first electrode apparatus such that the resulting measurement becomes independent of the transmitter current.

20. Material resistivity measuring apparatus as defined by claim 19 wherein the transmitter current is regulator to one of a discrete number of selectable levels and the phase of the modulated signal from the AC source has corresponding discrete values.

21. The material resistivity measuring apparatus as defined in claim 20 wherein adjacent current levels have corresponding phases which are separated by at least one phase corresponding to a nonadjacent current level to limit the effect of spurious signals.

22. The material resistivity measuring apparatus as defined in claim 21 wherein the number of discrete levels is eight.

23. The material resistivity measuring apparatus as defined in claim 22 wherein the eight phases of the first modulation are each separated by 45 degrees from the adjacent phase.

24. The material resistivity measuring apparatus as defined in claim 19 wherein a second modulation signal is applied to an input of the modulator at a frequency other than that of the first modulation signal to provide a reference phase for the receiver.

25. The material resistivity measuring apparatus as defined in claim 24 wherein the first modulation signal is at twice the frequency of the second modulation signal.

26. The material resistivity measuring apparatus as defined in claim 25 wherein the second modulation signal is 2 Hz and the first modulation signal is 4 Hz.

27. The material resistivity measuring apparatus as defined in claim 24 wherein the time over which the amplitude is averaged by the averaging apparatus contains an integer number of cycles of both the first and second modulation signals so that the modulations do not affect the measurement of the amplitude.

28. The material resistivity measuring apparatus as defined in claim 27 wherein the amplitude is averaged over one cycle of the second modulation.

29. The material resistivity measuring apparatus as defined in claim 20 wherein the transmitter includes a servo loop which uses an output of the first measuring apparatus as a feedback signal and controls the output of the power amplifier to regulate the current in the first electrode apparatus.

30. The material resistivity measuring apparatus as defined in claim 19 wherein the material is soil.

31. The material resistivity measuring apparatus as defined in claim 19 wherein the first and second electrode apparatus each comprises two electrodes.

32. The material resistivity measuring apparatus as defined in claim 31 wherein the electrodes of the first and second electrode apparatus are linearly aligned and the apparatus can be moved along the material surface.

* * * * *